(12) United States Patent
Utsumi et al.

(10) Patent No.: US 8,722,420 B2
(45) Date of Patent: May 13, 2014

(54) METHOD FOR DETECTING AN ENDOGENOUS BIOMOLECULE

(75) Inventors: Hideo Utsumi, Fukuoka (JP); Fuminori Hyodo, Fukuoka (JP); Kazuhiro Ichikawa, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 13/504,890

(22) PCT Filed: Oct. 29, 2010

(86) PCT No.: PCT/JP2010/069386
§ 371 (c)(1),
(2), (4) Date: Jul. 13, 2012

(87) PCT Pub. No.: WO2011/052760
PCT Pub. Date: May 5, 2011

(65) Prior Publication Data
US 2012/0276644 A1 Nov. 1, 2012

Related U.S. Application Data (60) Provisional application No. 61/256,059, filed on Oct. 29, 2009.

(51) Int. Cl.
*G01N 24/00* (2006.01)
(52) U.S. Cl.
USPC .............................. 436/173; 436/93; 424/9.3
(58) Field of Classification Search
None
See application file for complete search history.

(56) References Cited

U.S. PATENT DOCUMENTS

2008/0260649 A1 10/2008 Thaning et al.

FOREIGN PATENT DOCUMENTS

| JP | 2008-508267 A | 3/2008 |
| WO | 2006/011611 A2 | 2/2006 |

OTHER PUBLICATIONS

Lurie, D.J., Free Radical Imaging, 2001, the British Journal of Radiology, vol. 74, pp. 782-784.*
Rahman, K. Studies on free redicals, antioxidants, and co-factors, 2007, Clinical Interventions in Aging, vol. 2(2). pp. 219-236.*
Kenichi Yamada, Seitainai Redon Hanno no Mushinshu Kaisei o Mezashita Yugogata ESRI/MRI Sochi no Kaihatsu, Dai 16 Kai Bio Medical Bunseki Kagaku Symposium Koen Yoshishu, Aug. 2, 2003, pp. 112-113.
Kaiji Yasukawa, Reiko Miyakawa, Takashi Yao, Masazumi Tsuneyoshi, Hideo Utsumi, Non-invasive monitoring of redox status in mice with dextran sodium sulphate-induced colitis, Free Radical Research, May 2009; 43(5): 505-513.

(Continued)

*Primary Examiner* — Robert Xu
(74) *Attorney, Agent, or Firm* — Morgan, Lewis & Bockius LLP (57) ABSTRACT

Provided is a method for the real-time visualization of an endogenous biomolecule to clarify the mechanisms of various diseases and enable diagnosis and treatment of these diseases. Specifically provided is a novel method for visualizing an endogenous biomolecule by using a magnetic resonance method (including Overhauser MRI and the electron spin resonance method). The aforesaid visualization method, whereby an endogenous biomolecule is visualized on a real-time basis, comprises: a step for treating a living organism to be examined by a magnetic resonance method and thus acquiring data of the endogenous biomolecule; a step for processing the data of the endogenous biomolecule thus obtained to give imaging data; and a step for displaying the imaging data thus obtained.

2 Claims, 7 Drawing Sheets

(56) References Cited

OTHER PUBLICATIONS

Ken-Ichi Yamada, Ikuo Yamamiya, Hideo Utsumi, In vivo detection of free radicals induced by diethylnitrosarnine in rat liver tissue, Free Radical Biology & Medicine 40, 2006; 40(11): 2040-2046.

Mayumi Yamato, Toru Egashira, Hideo Utsumi, Application of in vivo ESR spectroscopy to measurement of cerebrovascular ROS generation in stroke, Free Radical Biology & Medicine, Dec. 15, 2003; 35(12):1619-31.

Hyodo et al., Assessment of tissue redox status using metabolic responsive contrast agents and Magnetic resonance imaging. The Journal of Pharmacy and Pharmacology. 2008, vol. 60, No. 8, pp. 1049-1060.

Ichkawa et al., Analysis of in vivo redox status with magnetic resonance technique, Yakugaku Zasshi 2009 vol. 129, No. 3, pp. 273-278.

Wang et al., Direct detection of circulating free radicals in the rat using electron spin resonance spectrometry. Free Radical Biology & Medicine, 1992. vol. 12, No. 2, pp. 121-126.

Extended European Search Report issued in the corresponding European Patent Application No. 10826890.5.

* cited by examiner a

CoQ

NADH

CoQ + NADH 0.5mT    FIG. 4A

OMRI images of an FAD semiquinone radical

FAD

Analysis of a mouse lower limb ischemia model, an animal model of arteriosclerosis obliterans, using a ubisemiquinone probe.

OMRI images after intramuscular administration of the ubisemiquinone probe (200μL was intramuscularly administered to its both limbs).

FIG. 7

METHOD FOR DETECTING AN ENDOGENOUS BIOMOLECULE

CROSS REFERENCE TO RELATED APPLICATIONS

This application claims priority under 35 U.S.C. 119 and 365 based upon U.S. Provisional Patent Application No. 61/256,059, filed on Oct. 29, 2009 and International Application No. PCT/JP2010/069386, filed on Oct. 29, 2010. The entire disclosure of the aforesaid application is incorporated herein by reference.

FIELD OF THE INVENTION

The present invention relates to a method for detecting in real time the oxidation and/or reduction reaction of endogenous biomolecules, more specifically to a method for detecting the oxidation and/or reduction reaction of endogenous molecules using an Overhauser MRI and/or an electron spin resonance (EPR) method.

BACKGROUND OF THE INVENTION

Endogenous molecules (substances) that form radical intermediates, i.e., having free radicals, such as ubiquinone (CoQ), vitamin K, ascorbic acid, or flavin adenine dinucleotide (FAD) and like, play an important role in the maintenance of constancy in vivo (homeostasis). In particular, being one of the electron carriers present in the inner membrane of the mitochondria that all cells have and/or in the cell membrane of prokaryotes, ubiquinone is deeply involved in the retention of mitochondrial function. For this reason, ubiquinone is expected to improve the intracellular mitochondrial function and to exhibit antioxidant and anti-aldosterone effects, and is also used as an adjuvant for cardiac function and the like.

Ubiquinone is a molecule involved in the transfer of electrons, called the Q cycle in mitochondrial respiratory chains I to III, and mediates electrons between the respiratory chain complexes I and III in the electron transfer system, thereby generating a semiquinone free radical in the process of a metabolism thereof. Free radicals such as this are related to an in vivo redox reaction. In vivo redox reaction is a concept which encompasses, in totality, the expression of a physiological functions mediated by an oxidation reduction reaction along with the production of active species thereof and the metabolism-reaction of the produced active species with biomolecules, which reaction has been suggested to be closely involved with a number of physiological phenomena and/or in vivo redox diseases that include cancer and diabetes.

Therefore, it is proposed that if there were a method available to directly visualize the behavior and modalities of the oxidation and/or reduction reaction of endogenous biomolecules such as ubiquinone, that would enable, from information on such endogenous molecules, in a variety of diseases, the elucidation of disease mechanisms, and diagnoses/treatments.

Conventional methods for in vivo imaging, such as this, include X-ray CT, PET, CT, magnetic resonance (MRI) and the like which have been conducted primarily for morphology imaging to perform spatial information imaging, but recently, in addition to morphology, functional imagining has come to be practiced which visualizes in vivo functions and phenomena.

For example, there is a case where a measurement is made by an electron spin resonance method, and the like, of free radicals generated in solution prepared from an isolated organ whereby a functional analysis is made from the changes in spectral waveform and its intensity, While that method allowed an in vitro level analysis, it has failed to show when, where, and how a substance in the body is associated with a given disease.

In addition, there is known a method for detecting-analyzing an in vivo oxidation reduction reaction that calls for administering to the body a synthetic nitroxyl radical compound as a probe, thereby using the compound's oxidation-reduction reaction as an indicator for the detection and analysis thereof However, that method which allows detection-analysis of the oxidation-reduction reaction in vivo, with the reaction of the synthetic nitroxyl radical compound as the indicator, has never been meant to directly detect and analyze the oxidation-reduction reaction of biomolecules.

PRIOR ART REFERENCES

Non-Patent References

Non-patent reference 1: Non-invasive monitoring of redox status in mice with dextran sodium sulphate-induced colitis. Yasukawa K, Miyakawa R, Yao T, Tsuneyoshi M, Utsumi H Free Radic Res. 2009 May; 43 (5): 505-13.
Non-patent reference 2: In vivo detection of free radicals induced by diethylnitrosamine in rat liver tissue. Yamada K, Yamamiya I, Utsumi H Free Radic Biol Med. 2006 Jun. 1; 40 (11):2040-6.
Non-patent reference 3: Application of in vivo ESR spectroscopy to measurement of cerebrovascular ROS generation in stroke. Yamato M, Egashira T, Utsumi H Free Radic Biol Med. 2003 Dec. 15;. 35 (12): 1619-31.

SUMMARY OF THE INVENTION

It is the problem of the present invention to provide a method to visualize in real time the oxidation and/or reduction reaction of an endogenous biomolecule so as to solve the problems mentioned above and enable elucidation of a mechanism thereof in various diseases and their diagnosis-treatment.

Specifically, the invention provides a novel detection method that visualizes the oxidation and/or reduction reaction of endogenous biomolecules using a magnetic resonance method (including Overhauser MRI (OMRI) and electron spin resonance). In other words, the detection method of the present invention is a method for detecting in real time an oxidation and/or reduction reaction of an endogenous molecule, comprising
a step of obtaining information on the endogenous biomolecule by applying a magnetic resonance method to a living body which is a subject to be measured; a step of obtaining imaging information by processing the information on the endogenous biomolecule; and a step of displaying the imaging information.

In addition, the magnetic resonance method as used in the detection method of the present invention may include an OMRI, electron spin resonance method, and the like. Use of these magnetic resonance methods allows collecting a more accurately measured image.

In addition, the endogenous biomolecules as endogenous molecular imaging targets in the detection method of the present invention may include, for instance, ubiquinone, vitamin K, ascorbic acid, or the FAD. Further, in the present invention, any endogenous substances may be targets for imaging as long as they have free radicals. The fact that these endogenous biomolecules can be imaged is important from the standpoint of making it possible to directly depict biological functions associated with these molecules in various diseases so as to elucidate the mechanism thereof and their diagnoses/treatments.

In addition, the endogenous biomolecules targeted in the detection method of the present invention may be those incorporated into the body from the outside thereof The detection method of the present invention now makes it possible to image in real time the oxidation and/or reduction reaction of endogenous biomolecules, culminating in performing, for the first time in the world, imaging, with Overhauser MRI, a semiquinone derived from the endogenous biomolecule ubiquinone. Particularly, with respect to ubiquinone, the ubiquinone semiquinone radical, when administered as an endogenous probe (contrast material) intrarectally to mice, showed that the ubisemiquinone radical decreased with time. Because the ubiquinone radical was stable in a solution state, this made it clear that the administered ubisemiquinone radical was decreased via an in vivo reaction.

Furthermore when ubisemiquinone was applied as a probe to a mouse lower limb ischemia model, an animal model for atherosclerosis obliterans, the disappearance of ubisemiquinone was significantly reduced compared to a control limb (normal side), demonstrating that this probe can monitor a pathological condition.

These results suggest that the present method can make it not only possible to visualize directly the oxidation and/or reduction reaction of endogenous biomolecules but also to visualize endogenous biomolecules themselves. Since the endogenous substance ubiquinone is utilized as a contrast agent, it is also expected to lead to a dramatic improvement from the viewpoint of the toxicity of the contrast agent.

Furthermore, use of the detection method of the present invention also led to a successful acquisition of OMRI images of a FAD semiquinone radical. Since FAD is utilized as an electron carrier in various organs in the living body, making use of FAD as an in vivo probe will permit its application to visualization of the redox (reaction) using the endogenous biomolecule.

DETAILED DESCRIPTION OF THE INVENTION

The present invention will be described in detail below. First, the endogenous biomolecules in the present invention is meant molecules (substances) that play an important role in the maintenance of constancy in vivo (homeostasis), that form radical intermediates, and that are originally present in the living body. They include specifically ubiquinone, vitamin K, ascorbic acid, flavin adenine dinucleotide (FAD), and vitamins B2 and the like These radicals that are generated have unpaired electrons and are paramagnetic and involved in in vivo redox reactions. The in vivo redox reaction is a concept which encompasses in totality the expression of physiological functions mediated by oxidation reduction reactions along with production of active species thereof and the metabolism/reaction of the produced active species with biomolecules, which reaction has been suggested to be closely related to a number of physiological phenomena and/or in vivo redox diseases that include cancer and diabetes. Therefore, the visualization of in vivo redox status can provide a new methodology for a minimally invasive disease mechanism analysis or for development of novel therapeutic drugs.

The detection method of the present invention is capable of offering accurate lag-free measured images such as redox dynamics images and/or in vivo functional images such as metabolism images, as functional images of the endogenous biomolecules and the like; and, tissue images (such as 13C, 1H, 31P nuclei) as morphological images and the like.

The magnetic resonance method used in the present invention is a general magnetic resonance method, one which makes use of a phenomenon (magnetic resonance) when a subject to be measured is subjected to an external electromagnetic wave or an oscillating magnetic field, it causes a type of resonance (magnetic resonance) to occur at a specific frequency and to strongly absorb the electromagnetic wave, whereby the frequency at which the resonance absorption occurs and/or absorption waveform allows measuring the states of the electrons and atomic nuclei inside the substance thereof. Specific examples of such magnetic resonance method include magnetic resonance imaging (MRI), Overhauser MRI (OMRI), nuclear magnetic resonance (NMR), electron spin resonance (EPR), and the like method. The measurement conditions for the magnetic resonance methods can be appropriately selected from within those commonly used for the respective modes of measurement.

For a device for imaging by magnetic resonance, use can be made of a device such as the one disclosed in International Publication Number: WO 2010/110384, i.e., a device comprising a magnetic-field generating means for generating a magnetic field to excite magnetic resonance in a subject to be measured;

a moving means for moving the subject to be measured or the magnetic-field generating means so as to move the subject to be measured through a magnetic field generated by the magnetic-field generating means;

a measurement means for applying a gradient magnetic field in either one direction or both directions, a moving direction y in which the subject to be measured moves relative to the magnetic-field generating means and a direction x perpendicular to the moving direction y thereby obtaining measured image signals in the subject to be measured, without stoppage during the motion by the moving means, by means of either phase-encoding or frequency-encoding, or both; and a correction means for correcting the measured image signals for the influence of movement in the y-direction.

Herein, the magnetic-field generating means may include a first magnetic field generating means for generating a predetermined intensity, and a second magnetic field generating means for generating a magnetic field having an intensity different from the intensity of the first magnetic field generating means; and the moving means may move either the subject to be measured or the first and second magnetic field generating means, thereby sequentially moving the subject to be measured through magnetic fields generated by the first and second magnetic field generating means In addition, the moving means may be a rotationally moving means of rotationally moving the subject to be measured or the first and second magnetic generating means, thereby passing the subject to be measured in sequence through the magnetic fields generated by the first and second magnetic generating means.

Information on the endogenous biomolecules can be obtained by applying the magnetic field generating means to the moving subject to be measured in this way. Herein, for example, in order to obtain redox dynamic images, one of the first or second magnetic field generating means may be used to measure by exciting a nuclear magnetic resonance, and the other may be for exciting an electron spin resonance for a measurement. This makes it possible to obtain an accurate lag-free in vivo redox dynamics image.

Any one of the first and second magnetic field generating means may generate a magnetic field having a higher intensity than the other. If the second magnetic field generating means is designed to generate a magnetic field having an intensity higher than that generated by the first magnetic field generating means, the first magnetic field generating means generating a magnetic field having a lower intensity may be employed as an apparatus for exciting electron spin for carrying out OMRI, and the second magnetic field generating means generating a magnetic field having a higher intensity may be employed as an apparatus for generating an external magnetic field for an MRI and OMRI. Thus, the second magnetic field generating means provides MRI images and OMRI images.

On the other hand, if the first magnetic field generating means is designed to generate a magnetic field having an intensity higher than that generated by the second magnetic field generating means, for example, the first magnetic field generating means generating a magnetic field having a higher intensity may be employed as an apparatus for generating an external magnetic field for an MRI, and the second magnetic field generating means generating a magnetic field having a lower intensity may be employed as an apparatus for generating an external magnetic field for an OMRI. Thus, the first magnetic field generating means provides MRI images and the second magnetic field generating means provides OMRI images.

In the step of obtaining the imaging formation by processing the information on the endogenous biomolecule obtained above, a corrected image signal is obtained by correcting the information on the endogenous biomolecule obtained above (measured result) for the influence of the moving of the subject to be measured. The corrected signals (imaging information), in which $S(k_x, k_y)$ is the measured image signal and $S'(k_x, k_y)$ is the corrected signals, may be obtained in accordance with the following equation:

$$S'(k_x, k_y) = \exp\left[\frac{i}{2\pi}\gamma G_y^{(n)}\left\{\frac{v_y}{2}\Delta t_y + v_y t_{y0}\right\}\Delta t_y\right]S(k_x, k_y)$$

(wherein $k_x$, $k_y$ are the spatial frequencies in the directions x and y respectively; $\gamma$ is the gyromagnetic ratio; $G_y^{(n)}$ is is the intensity of the gradient magnetic field of the phase-encoding or the frequency-encoding in an n-th measurement; $v_y$ is the moving velocity in the moving direction y; $\Delta t_y$ is the period of time during which the phase-encoding or the frequency-encoding is applied; $t_{y0}$ is the period of time until the phase-encoding or the frequency-encoding starts being applied).

The corrected signals, in which $S(k_x, k_y, k_z)$ is the measured image signal and $S'(k_x, k_y, k_z)$ is the corrected signals, may be obtained in accordance with the following equation:

$$S'(k_x, k_y, k_z) = \exp\left[\frac{i}{2\pi}\gamma G_y^{(n)}\left\{\frac{v_y}{2}\Delta t_y + v_y t_{y0}\right\}\Delta t_y\right]S(k_x, k_y, k_z)$$

(wherein $k_x$, $k_y$, and $k_z$ are the spatial frequencies in the directions x, y, and z respectively; $\gamma$ is the gyromagnetic ratio; $G_y^{(n)}$ is the intensity of the gradient magnetic field of the phase-encoding or the frequency-encoding in an n-th measurement; $v_y$ is the moving velocity in the moving direction y; $\Delta t_y$ is the period of time during which the phase-encoding or the frequency-encoding is applied; $t_{y0}$ is the period of time until the phase-encoding or the frequency-encoding starts being applied.

The imaging information obtained above is displayed on a display unit such as a monitor, making it possible to observe in real time endogenous biomolecules themselves and/or the reactions in which endogenous biomolecules themselves are involved.

Below, the effects of the present invention are explained with examples. However, it is unnecessary to state that the present invention is not limited to the examples described below and that various changes and modifications are included within the scope of the present

EXAMPLE 1

Phantom Experiment

Figure 3A:
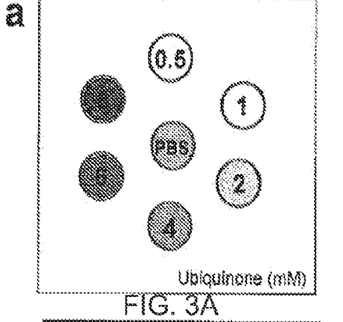
FIGS. 3A to 3D are figures show in vitro molecular imaging of ubisemiquinone radicals with OMRI.

A phantom consisting of 7 tubes were used in which each tube (4.7 mm id) contained 0, 0.5, 1, 2, 4, 6, or 8 mM aqueous ubiquinone solution (pH11.8) (See FIG. 3a). In the ubiquinone/NADH phantom experiment, both reagents are dissolved in the phosphate buffer (PBS)(pH7.4). An NADH solution (final concentration: 50 mM) was added into the ubiquinone solution (Final concentration: 10 mM, followed by OMRI imaging. The results are shown in FIG. 4.

The OMRI experiments were performed using a custom-made human whole-body magnet (79 cm diameter; 125cm length) (the Philips Research Laboratories in Hamburg) operating in a field-cycle mode so as to avoid excess power during the EPR cycle. The EPR $B_0$ was at 8.1 mT, the NMR B0 was 15 mT. The resonator assembly for the mice experiments was tuned to 625 kHz and with a bandwidth of 80 kHz; it consists of the NMR transmit saddle coil (25 cm diameter, 23 cm length) and a solenoidal receiving coil (2.5 cm diameter, 60 mm length). The maximum transmit power is 250 W (peak). For EPR, a saddle coil (13.5 cm, 23.5 cm length) tuned to 220.6 MHz and NMR coils are used. The maximum transmit power is 100 W.

The OMRI experiments were performed using a standard gradient-echo type sequence for MRI. The phase encoding step was preceded by an EPR saturation pulse to elicit the Overhauser effect (hyperpolarization). A 600 ms pulse at a given power was used for the experiment. The pulse sequence was started from the B0 field to 8.1 mT, which corresponded to the EPR irradiation. This was followed by the EPR irradiation (220.6 MHz) for a period of about 200 ms, and the B0 field reached 15 mT before the field gradients associated with the radiofrequency (RF) pulse were ON. The images were reconstructed from the echoes using standard software and were stored in DICOM (Digital Imaging and Communication in Medicine). General scan conditions in OMRI are TEPR× TR×TE=600 ms×1200 ms×25 ms; No. of averages=1, 64 phase-encoding steps.

The imaging field (phantom 28 mm, in vivo 48 mm) is a 64×64 size.

EXAMPLE 2 in vivo OMRI imaging

C57BL6 mice (female, 5 weeks of age) were purchased from Nippon SLC, Inc., (Hamamatsu, Japan) and were acclimated for one week before the experiment. The mice were housed 5 mice per cage in a temperature- and circadian-rhythm-controlled room with uninterrupted water and feeding; they were 6 to 8 weeks of age and had body weights, 20 to 30 g at the time of the experiment. All procedures and animal care were approved by the Committee on Ethics of Animal Experiments, Faculty of Pharmaceutical Sciences, Kyushu University, and were conducted according to the Guidelines for Animal Experiments of the Faculty of Pharmaceutical Sciences, Kyushu University.

Mice were anesthetized with (2 g/kg) urethane and were immobilized with the stomach side down to a holder using a dermatological adhesive tape. The body temperature of mice during the experiment was 37±1° C. The mice were transferred to the resonator to start an OMRI measurement. The OMRI imaging of the lower abdomen area was made immediately after a rectal administration of an aqueous 8 mM ubiquinone solution (800 µL) that had been adjusted to pH11.8. The OMRI conditions are as follows. TR, 1200 ms; TE, 25 ms; TEPR, 600 ms; number of phase-encoding gradient steps, 64; NEX, 4; FOV, 48 mm×48 mm; Matrix size, 64×64 (in-plane resolution 0.75 mm); slice thickness, 30 mm; number of average, 1, scanning time, 79 s. The OMRI data were analyzed using Image J software package (http://rsb.info.nih.gov/ij/).

EXAMPLE 3

Molecular Imaging of Flavin Adenine Dinucleotide (FAD) by OMRI

Flavin adenine dinucleotide (FAD), an in vivo electron carrier, is a cofactor needed in an oxidation-reduction reaction in several metabolic reactions. FADH2 is an energy carrier; a reduced coenzyme is used as a substrate for mitochondrial oxidative phosphorylation. Such FAD was dissolved in PBS (pH7.4) to prepare aqueous FAD solutions thereof at various concentrations Then, after the addition of an aqueous NADH solution of a concentration equal to that of FAD, OMRI imaging was performed. The results are shown in FIG. 6.

EXAMPLE 4

Figure 7:
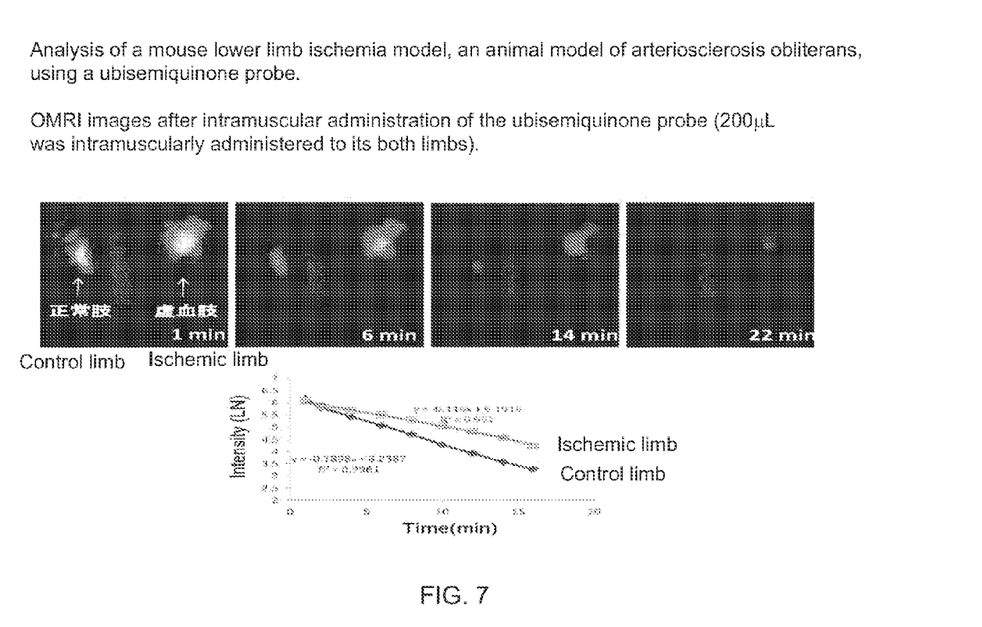
FIG. 7 is a figure showing the analytical results, using a ubisemiquinone probe, of a mouse lower limb ischemia model, an animal model of arteriosclerosis obliterans.

Under isoflurane anesthesia (2%), a right lower limb ischemia model was prepared by ligation of the mouse aorta. The OMRI measurement was performed 24 hours after the ischemia. Surgery was performed on the control limb in a manner similar to that of the ischemic limb, with the only exception being not ligating it. A 100 mM NADH was added to an aqueous 50 mM ubiquinone solution; 200 µL of the resultant mixed solution 10 minutes later was administered intramuscularly to both limbs of a mouse, followed by immediately starting an OMRI measurement. The results are shown in FIG. 7.

[Results]

Figure 1A:
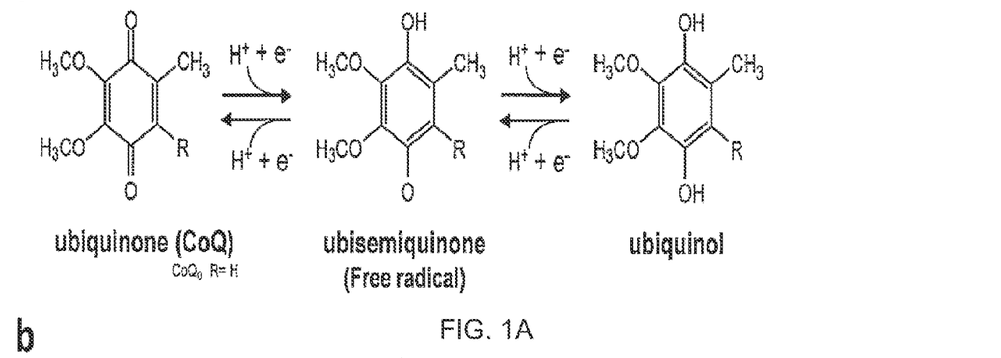
FIG. 1A is a figure showing the scheme of ubiquinone oxidation-reduction reaction.

FIG. 1a shows the scheme of ubiquinone oxidation-reduction in the mitochondrial respiratory chain (Complex I). Ubiquinone accepts two electrons from NADH and is converted to ubiquinol via the ubisemiquinone radical form, in which an electron spin resonance spectrum can be detected. The benzoquinone derivative sites involved in the oxidation-reduction of ubiquinone have para-oxygen atoms; C2 has a methyl group, and C4 and C5 each has a methyl group via an oxygen atom. C3 has an isoprene side chain attached thereto, forming a long carbon chain so as to be retained in a biomembrane. The structure is shown in the figure below.

The number of isoprene side chains (n=) is 10 in higher, and 6 to 9 in the lower animals, where the longer the isoprene side chain the greater the tendency to turn yellowish orange in color. Incidentally, a ubiquinone with n=10 is "UQ10" showing the number of the isoprene side chains such that coenzyme Q10, used as a cosmetic material, means that the number of isoprene side chains is 10.

Figure 1B:
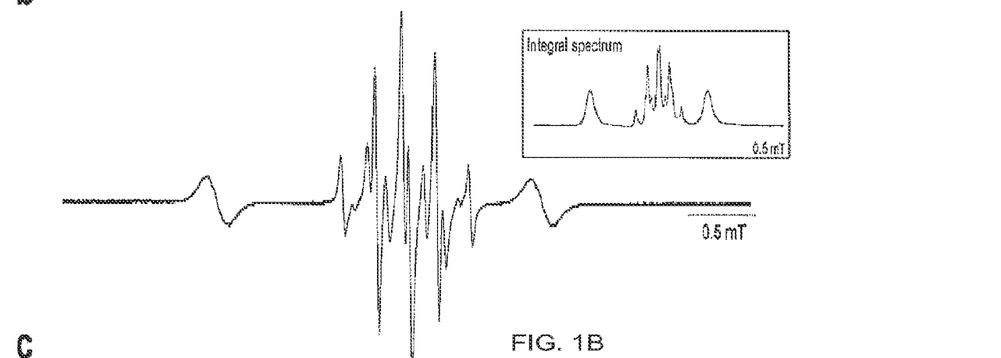
FIG. 1B, an EPR spectrum of a ubisemiquinone radical.

The electron spin resonance spectrum of a ubisemiquinone radical shown in FIG. 1b was produced by 8 mM ubisemiquinone at pH11.8, as adjusted with aqueous 1N sodium hydroxide solution. Electron spin resonance spectra detected in front and back thereof were produced by 1 mM 15N-CAT1, an internal standard. 15N-CAT1 was synthesized on the basis of the 14N-CAT1.

Figure 1C:
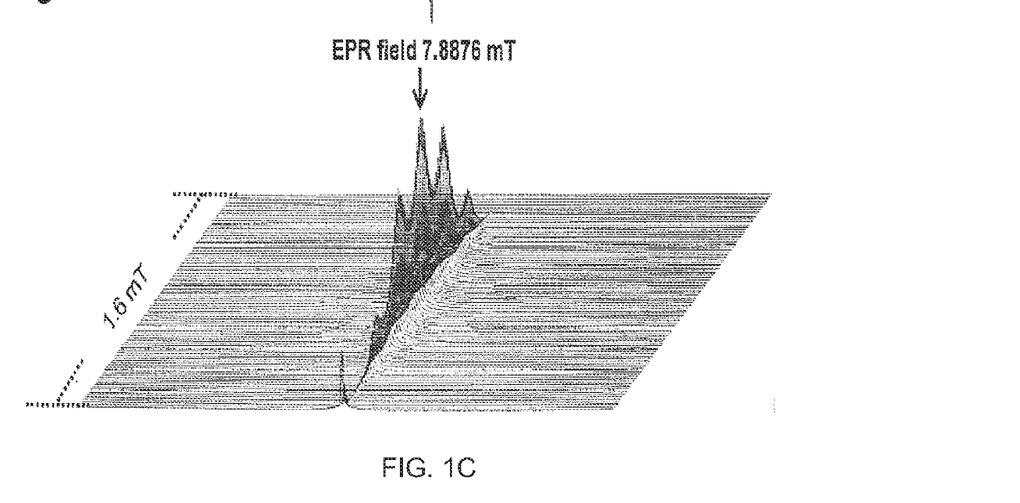
FIG. 1C, a DNP spectrum of a ubisemiquinone radical respectively.

FIG. 1C shows the dynamic nuclear polarization (DNP) spectrum of a ubisemiquinone radical. This was obtained using the Overhauser effect (OMRI) apparatus. A 100-step scanning with a sweep width of 1.6 mT was carried out (0.016 mT/scan). The magnetic field for the electron spin resonance irradiation of the OMRI apparatus used was 7,887 mT. The conditions for the electron spin resonance and Overhauser effect MRI were as follows: EPR: microwave power, 1 mW field modulation frequency, 100 kHz; magnetic field modulation amplitude, 0.002 mT; irradiation time, 0.03 seconds; sweep width, 5 mT; OMRI: TR (repetition time) 1200 ms; TE (echo time), 25 ms; and TEPR, 600 ms.

Figure 2A:
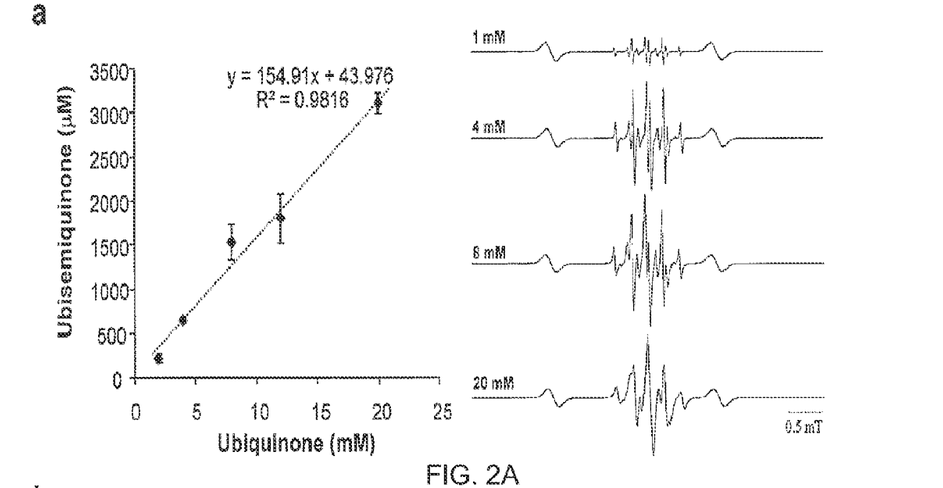
FIG. 2A is a graph showing the ubiquinone concentration dependency of semiquinone radical production, and ubisemiquinone EPR spectra at each concentration.
Figure 2B:
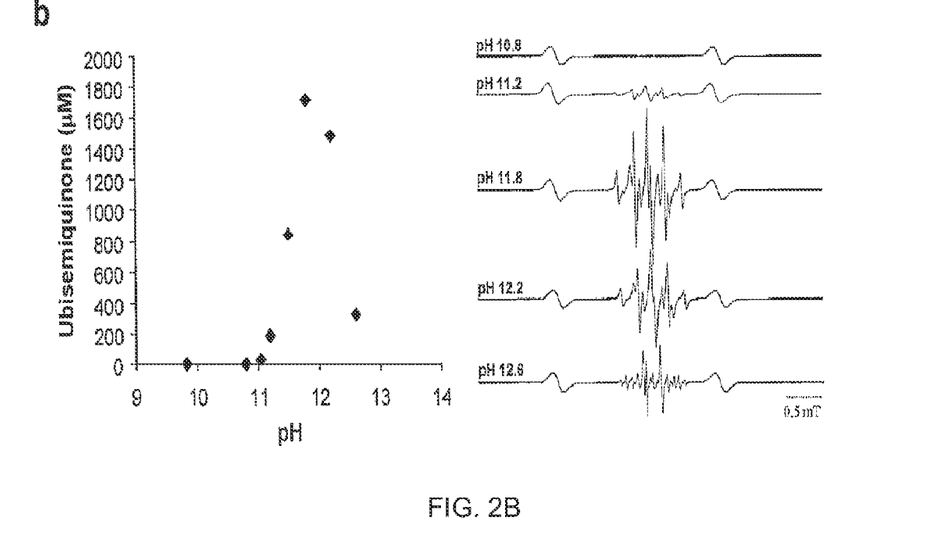
FIG. 2B is a figure showing the pH dependency of semiquinone radical production, and ubisemiquinone EPR spectra at each pH.

FIG. 2 shows the concentration and pH dependencies in the ubisemiquinone radical production. FIG. 2A shows the concentration-dependency (left) and electron spin resonance spectra (right), which were measured using 8 mM ubiquinone at pH 11.8, adjusted with aqueous1N sodium hydroxide solution. The ubiquinone concentrations were set to 1, 2, 4, 8, 12 and 20 mM. All measurements were repeated three times with aqueous solutions freshly prepared just before use. Ubisemiquinone is produced in proportion to the increase in the ubiquinone concentration, showing that this is a concentration dependent reaction.

FIG. 2B is a scattered plot diagram of pH dependency. It shows the concentration of ubisemiquinone produced from 8 mM ubiquinone with its pH adjusted to 9.84, 10.8, 11.0, 11.2, 11.5, and 12.2 using aqueous1N sodium hydroxide solution (left diagram). In addition, as a result of conducting X-band electron spin resonance measurements after each pH adjustment for 10 minutes (shown at right), the maximum signal intensity was obtained with the aqueous ubiquinone solution adjusted to pH11.8. However, under conditions of pH 10.8 or lower, no electron spin resonance signals were obtained. The EPR measurement conditions were: microwave power, 1 mW; magnetic field modulation frequency, 100 kHz; magnetic field modulation amplitude, 0.002 mT; irradiation time, 0.03 seconds; sweep width, 5 mT.

FIG. 3 shows the results of in vitro molecular imaging of ubisemiquinone radical with OMRI. FIG. 3A shows a schematic diagram of the phantoms used. Numerical values represent the concentrations of ubiquinone radical in aqueous solutions (0. 5, 1, 2, 4, 6, and 8 mM), which were adjusted to pH11.8 with aqueous 1N sodium hydroxide solution Each aqueous ubiquinone radical solution was filled in glass tubes (diameter 4 mm, height, 30 mm) for the measurements.

Figure 3B:
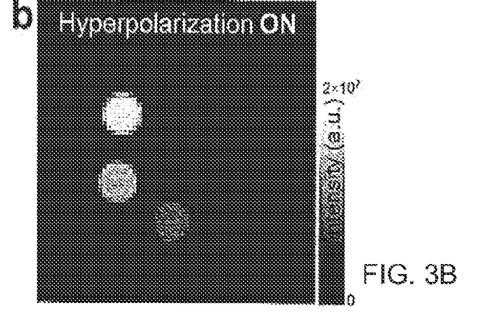
Figure 3C:
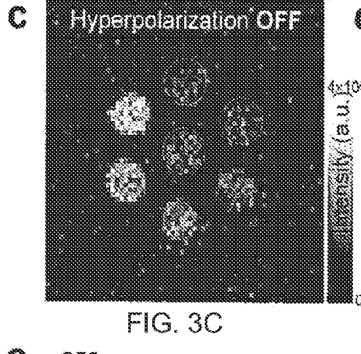

FIG. 3B shows the OMRI images of the phantoms with EPR irradiation on (Hyperpolarization ON), and in FIG. 3C, those for EPR irradiation off (Hyperpolarization OFF). Under conditions of EPR irradiation OFF, the OMRI acquisition sensitivity was low, but image data of a ubisemiquinone radical produced from 8 mM ubiquinone were acquired in an OMRI imaging method (EPR ON) with an EPR irradiation on for a nuclear spin enhancement.

Figure 3D:
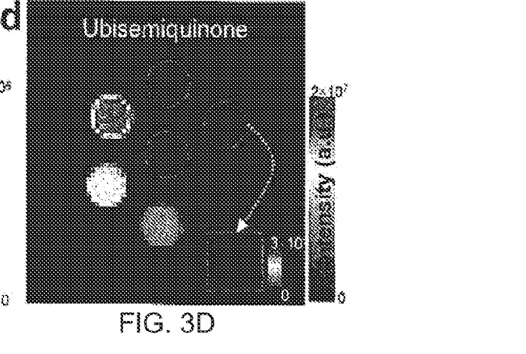
Figure 3E:
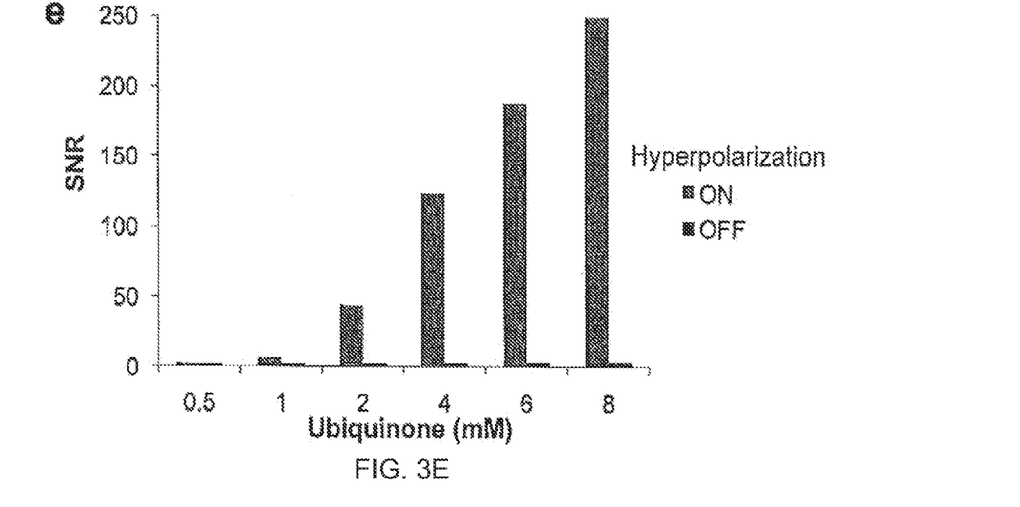
FIG. 3E, the differences in signal intensity with EPR irradiation ON and OFF.

FIG. 3D shows a subtraction image obtained by subtraction of the EPR irradiation OFF image data from the EPR irradiation ON image data; FIG. 3E shows the differences in SNR signals with the EPR irradiation ON or OFF. These results have verified that adjusting the aqueous solution to be alkaline make it possible to acquire electron spin resonance spectra and OMRI image data of a ubisemiquinone radical. In order to further analyze an in vivo redox status, a measurement system using an electron donor was constructed.

FIG. 4 shows the results of a spectral analysis and molecular imaging of a ubisemiquinone radical in the CoQ/NADH system using EPR and OMRI. Here were obtained electron spin resonance spectra and OMRI imaging of a ubisemiquinone radical produced under in vivo pH conditions with addition of NADH, an electron donor.

Figure 4A:
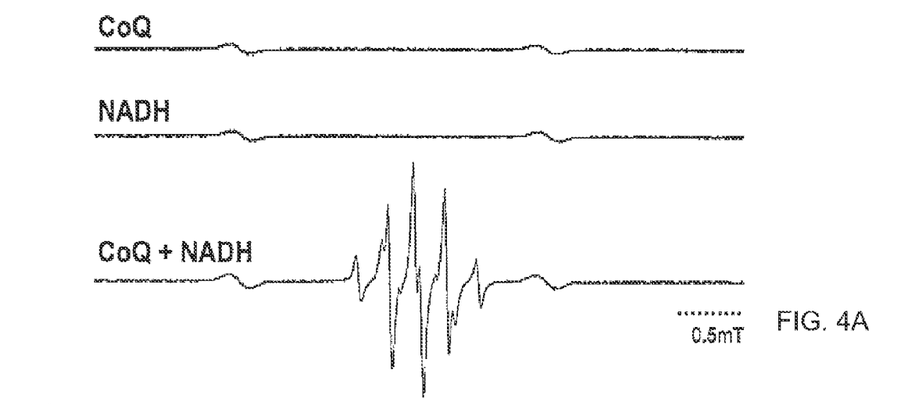
FIG. 4A is a figure for the EPR spectra of coenzyme Q-0 (CoQ0), NADH, and a mixture of CoQ0 and NADH.
Figure 4B:
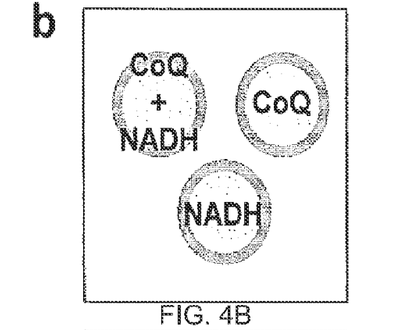
FIGS. 4B to 4E, the molecular imaging of a ubisemiquinone radical.
Figure 4C:
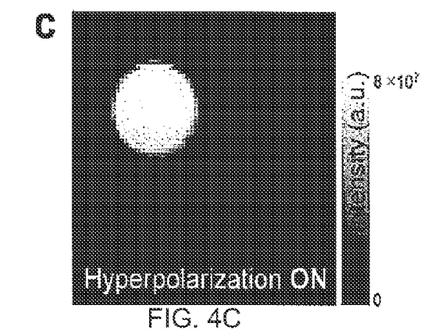
Figure 4D:
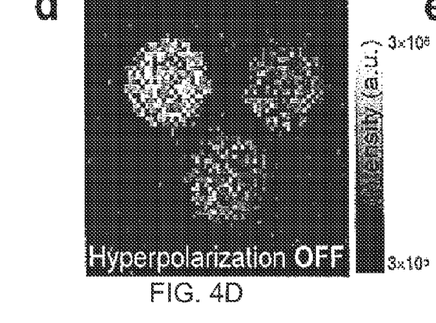
Figure 4E:
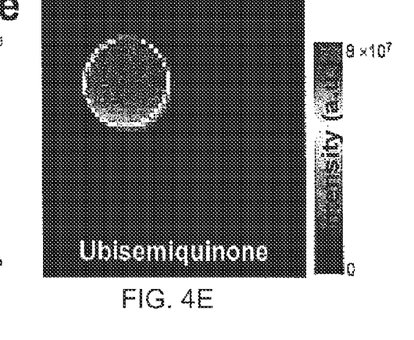

FIG. 4A shows electron spin resonance spectra of 10 mM coenzyme Q-0 (Co-Q0: the number of isoprene side chains is 0), 50 mM NADH, and a mixture of 10 mM of CoQ-0 and 50 mM NADH, all dissolved in PBS adjusted to pH 7.4. FIG. 4B shows a schematic diagram of phantoms arrangement of a ubisemiquinone radical. FIGS. 4C and 4D are respectively for OMRI images of such ubiquinone radical subjected to electron spin resonance (Hyperpolarization OFF) and not subjected thereto (Hyperpolarization OFF). FIG. 4E is the ubisemiquinone radical image data obtained from a subtraction data of Hyperpolarization OFF from Hyperpolarization ON, verifying from these results that it is possible to acquire electron spin resonance spectra and OMRI image data of the ubisemiquinone radical produced under conditions involving addition of NADH, an electron donor, thereto.

Figures 5A, 5B, 5C, 5D:
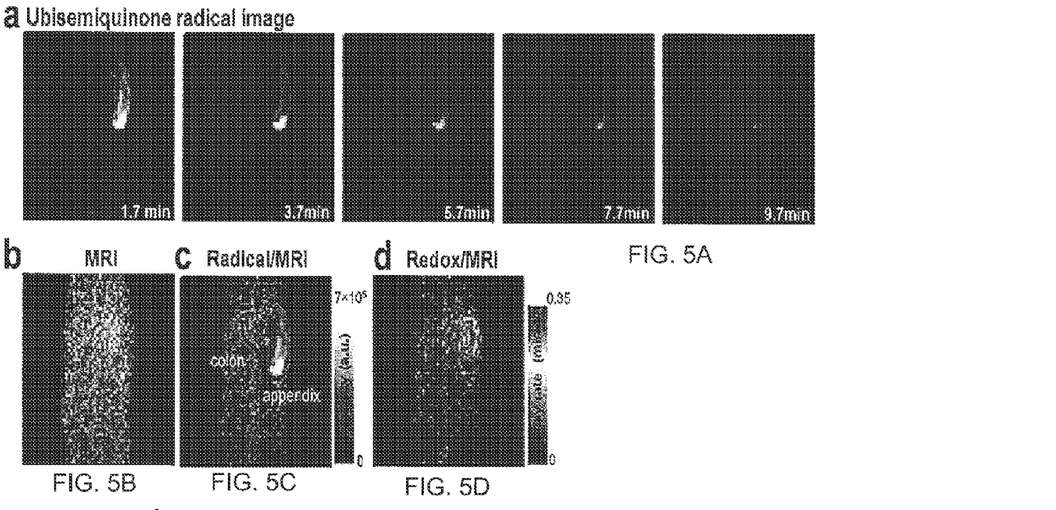
FIGS. 5A to 5D are figures showing in vivo molecular imagings of ubisemiquinone radical.
Figure 5E:
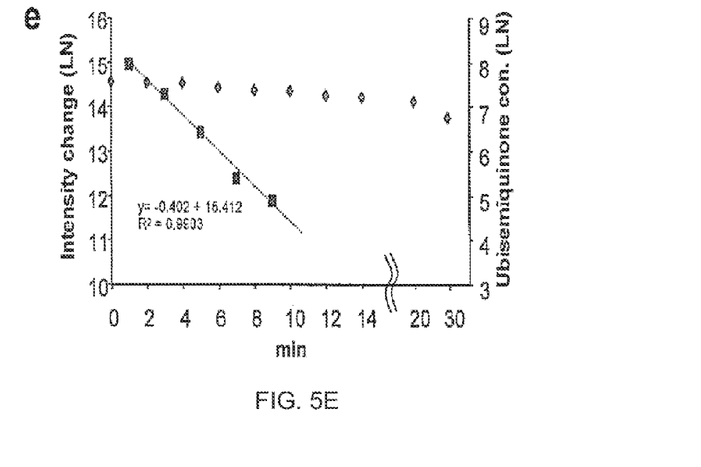
FIG. 5E, a graph showing a change with time of OMRI signals in the appendix.

FIG. 5 shows the result of evaluating the performance of an in vivo OMR imaging of wild-type mice administered intrarectally with a ubisemiquinone radical. FIG. 5A shows the metabolic dynamics of a ubisemiquinone radical in the mouse large intestine and appendix. FIG. 5B shows a proton MR image of a mouse (in vivo imaging data) (Hyperpolarization-OFF); FIG. 5C, a fused image data of images of a proton MR and a ubisemiquinone free radical; FIG. 5D, a redox map and an MRI image, respectively. The redox map is a semilogarithmic plot of the calculated ubisemiquinone free radical disappearance rate constant per pixel of a ubisemiquinone free radical imaging data. Further, FIG. 5E is a semilogarithmic plot of the time course of the MRI signal in the appendix and the stability of an aqueous ubiquinone solution.

The OMRI image intensities of the large intestine and the appendix are shown to gradually decrease with the disappearance of the ubisemiquinone free radicals (a). While the OMRI image intensities of the large intestine and appendix gradually decreased per the disappearance of ubisemiquinone free radicals, the intensity of the aqueous ubiquinone solution was stable for not less than 20 minutes. These data demonstrate that a ubisemiquinone free radical is produced from the aqueous ubiquinone solution administered in vivo by an in vivo redox reaction thereof and that the data are imaging its in vivo dynamics.

Figure 6A:
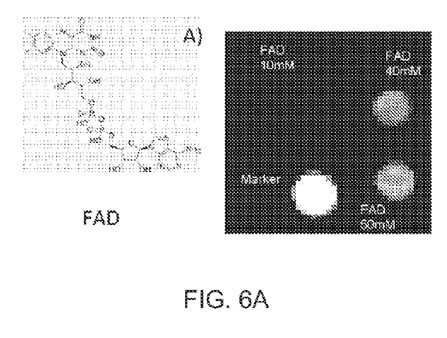
FIG. 6A is a figure showing the OMRI images of a FAD semiquinone.
Figure 6B:
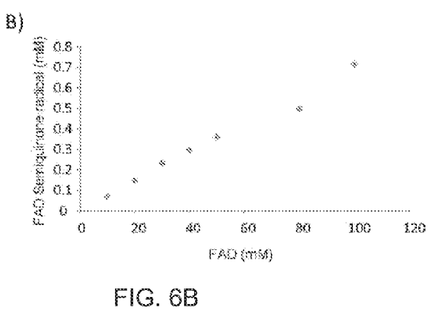
FIG. 6B is a graph showing the relationship between the FAD concentration and FAD semiquinone radical concentration.

FIG. 6 shows the results of molecular imaging by OMRI of flavin adenine dinucleotide (FAD). Irradiation of the central magnetic field of the FAD's ESR spectrum as an OMRI electron spin excitation magnetic field provided OMRI images of an FAD semiquinone radical. As a result of quantification with ESR of prepared 10 mM to 100 mM aqueous solutions to which were similarly added equimolar amounts of NADH, it became evident, as exhibited in FIG. 6B, that the semiquinone radicals are produced depending on the FAD concentration. Use of FAD, which functions as an electron carrier in the organs in vivo, makes it possible to visualize redox reactions with endogenous biomolecules.

FIG. 7 shows analytical results of the use of a ubisemiquinone probe with a mouse lower limb ischemia model, an animal model of arteriosclerosis obliterans. After having the ubisemiquinone probe administered, images of a ubisemiquinone distribution in both of the mouse's limbs were obtained, as shown in FIG. 7. Image intensity in the ischemic limb was higher than in a control limb. With a selection of a respective region as the region of interest in the image intensity, a change in the intensity was plotted, where the disappearance of the probe in the ischemic limb was significantly slower compared to that of the control limb. This shows that the radical disappearance capability of the ubiquinone probe has significantly diminished due to a muscular tissue impairment caused by ischemia. These results demonstrate that the probe is capable of monitoring a redox function impairment in in vivo tissues.

We claim:

1. A method for detecting in real time an oxidation and/or reduction reaction of an endogenous molecule, comprising steps of:
   obtaining information on the endogenous biomolecule by applying a magnetic resonance method to a living body which is a subject to be measured;
   obtaining imaging information by processing the information on the endogenous biomolecule; and
   displaying the imaging information;
   wherein the step of obtaining information on the endogenous biomolecule is that of obtaining: (i)information on ubiquinone, flavin adenine dinucleotide, vitamin K, or ascorbic acid in the subject to be measured; or (ii) information on ubiquinone, flavin adenine dinucleotide, vitamin K, or ascorbic acid in a sample obtained from the living body as the subject;

the subject or the sample has been preliminarily administered with NADH and the endogenous biomolecule; and
the magnetic resonance method is either an Overhauser Magnetic Resonance Imaging (MRI) method or an electron spin resonance method.

2. The method as set forth in claim 1, wherein the endogenous biomolecule is incorporated in the living body from the outside thereof.

* * * * *